United States Patent
Nackvi

(10) Patent No.: US 9,036,825 B2
(45) Date of Patent: May 19, 2015

(54) AUDIO SIGNAL CORRECTION AND CALIBRATION FOR A ROOM ENVIRONMENT

(71) Applicant: Fawad Nackvi, Collin, TX (US)

(72) Inventor: Fawad Nackvi, Collin, TX (US)

(73) Assignee: AMX LLC, Richardson, TX (US)

(*) Notice: Subject to any disclaimer, the term of this patent is extended or adjusted under 35 U.S.C. 154(b) by 343 days.

(21) Appl. No.: 13/710,690

(22) Filed: Dec. 11, 2012

(65) Prior Publication Data

US 2014/0161281 A1 Jun. 12, 2014

(51) Int. Cl.
| | |
|---|---|
| H04B 3/20 | (2006.01) |
| H03G 5/16 | (2006.01) |
| H03F 1/06 | (2006.01) |
| H03F 3/181 | (2006.01) |
| H03F 3/189 | (2006.01) |
| H03F 3/66 | (2006.01) |
| H04R 1/20 | (2006.01) |
| H04R 1/22 | (2006.01) |
| H04R 1/24 | (2006.01) |
| H04R 1/26 | (2006.01) |
| H04R 3/04 | (2006.01) |
| H04R 9/18 | (2006.01) |
| H04R 11/14 | (2006.01) |
| H04R 15/02 | (2006.01) |

(Continued)

(52) U.S. Cl.
CPC ............ *H03G 5/165* (2013.01); *H03F 1/06* (2013.01); *H03F 3/181* (2013.01); *H03F 3/189* (2013.01); *H03F 3/66* (2013.01); *H04R 1/20* (2013.01); *H04R 1/22* (2013.01); *H04R 1/227* (2013.01); *H04R 1/24* (2013.01); *H04R 1/26* (2013.01); *H04R 3/04* (2013.01); *H04R 9/18* (2013.01); *H04R 11/14* (2013.01); *H04R 15/02* (2013.01); *H04R 17/10* (2013.01); *H04R 25/353* (2013.01); *H04R 25/48* (2013.01); *H04R 25/558* (2013.01); *H04S 7/307* (2013.01); *A61F 2002/765* (2013.01); *H03F 2200/333* (2013.01); *H03F 2200/348* (2013.01); *H03F 2200/429* (2013.01); *H03F 2200/451* (2013.01); *H03F 2203/45264* (2013.01); *H04R 2201/028* (2013.01); *H04R 2205/021* (2013.01); *H04R 2205/026* (2013.01); *H04R 2227/005* (2013.01); *H04S 2400/07* (2013.01)

(58) Field of Classification Search
None
See application file for complete search history.

(56) References Cited

U.S. PATENT DOCUMENTS

| | | | |
|---|---|---|---|
| 6,760,451 B1 * | 7/2004 | Craven et al. | 381/98 |
| 7,158,643 B2 * | 1/2007 | Lavoie et al. | 381/58 |

(Continued)

OTHER PUBLICATIONS

Sbragion, Denis, "DRC: Digital Room Correction", Oct. 1, 2012, http://drc-fir.sourceforge.net/doc/drc.html.

(Continued)

*Primary Examiner* — Brenda Bernardi

(57) ABSTRACT

Disclosed are an apparatus and method of processing an audio signal to optimize audio for a room environment. One example method of operation may include recording the audio signal generated within a particular room environment and processing the audio signal to create an original frequency response based on the audio signal. The method may also include identifying a target sub-region of the frequency response which has a predetermined area percentage of a total area under a curve generated by the frequency response, determining whether the target sub-region is a narrow energy region, creating a filter to adjust the frequency response, and applying the filter to the audio signal.

20 Claims, 19 Drawing Sheets

(51) Int. Cl.
  *H04R 17/10* (2006.01)
  *H04R 25/00* (2006.01)
  *H04S 7/00* (2006.01)
  *A61F 2/76* (2006.01)

(56) References Cited

U.S. PATENT DOCUMENTS

| | | |
|---|---|---|
| 7,529,377 B2 | 5/2009 | Nackvi |
| 7,567,675 B2 | 7/2009 | Bharitkar et al. |
| 7,664,276 B2 * | 2/2010 | McKee Cooper ............ 381/103 |
| 2005/0063554 A1 * | 3/2005 | Devantier et al. ............. 381/99 |
| 2007/0121955 A1 * | 5/2007 | Johnston et al. ............. 381/56 |
| 2008/0069378 A1 * | 3/2008 | Rabinowitz et al. ......... 381/103 |
| 2010/0272270 A1 * | 10/2010 | Chaikin et al. ............... 381/59 |
| 2011/0311065 A1 * | 12/2011 | Horbach et al. .............. 381/58 |
| 2012/0288124 A1 * | 11/2012 | Fejzo et al. ................. 381/303 |

OTHER PUBLICATIONS

"Transfer Function Modeling and Equalization by Fixed-Pole Parallel Filters", Mar. 31, 2011, http://home.mit.bme.hu/~bank/parfilt/.

* cited by examiner

130

140

800

| FREQUENCY (1 OCTAVE) | NUMBER OF MODES |
|---|---|
| 20 - 40 Hz | 0 |
| 40 – 80 Hz | 5 |
| ... | |
| 100 – 200 Hz | 46 |
| ... | |
| 2500 – 5000 Hz | 350 |

FIG. 8

AUDIO SIGNAL CORRECTION AND CALIBRATION FOR A ROOM ENVIRONMENT

TECHNICAL FIELD OF THE INVENTION

This invention relates to a method and apparatus of performing audio correction and calibration for a reverberant room environment to reduce feedback and optimize audio capabilities.

BACKGROUND OF THE INVENTION

All audio systems are affected by the environment or room in which they are installed. For example, digital audio sources, such as compact discs and other types of discs (e.g., CDs and DVDs) have a +/−0.001 dB flat frequency response from 20 Hz to 20 kHz. Such audio sources also have a high S/N ratio of >100 dB, and negligibly low distortion levels of THD 0.001% at full scale. In addition, the digital signals are free from transient distortion, reverberation as well as 'wow' or 'flutter'. However, when such high quality CDs or DVDs are played in a typical room, the room modifies the signal heard by the listener from what was originally intended. The speaker is responsible for some frequency deviation from the flat response and increased distortion but the room still has the largest affect on the audio quality.

A typical room can change a flat frequency response by greater than 40 dB. The highest affect is generally at the lower frequencies, such as below 300 Hz or more (i.e., Schroeder's frequency), when room modes are created. However, at higher frequencies reflections from walls, ceilings and floors cause not only frequency distortion but reverberation and in extreme cases a discrete echo can be heard.

The low frequency room modes can also cause very slow decay of sound notes which masks sounds near its frequency, which reduces the sound quality and intelligibility. As the effect is so dramatic on the audio, a number of attempts have been made to improve sound quality. A known conventional 'solution' is to adjust the room dimensions such that the height to width and height to length ratio is not an integer. However, this is not possible if the room has already been designed. Other conventional solutions may be to treat the room with sound absorbers, baffles and bass traps as is done in recording studios. However, this can be very expensive to do or may not be viable when the room is a conference room or a room used for multiple purposes or living in general.

The earliest attempts at room correction used graphic equalizers. The most sophisticated graphic equalizers were ⅓ octave (33-bands). As the quality (Q) for ⅓ octave is only 4.3 this Q is clearly not high enough to correct the room modes. Also, the frequency overlapping nature of the 33-band graphic equalizer makes it difficult to dial-in a correction. Later DSP based attempts at room correction involved inverting the room response. This approach would clearly require a huge processing task as the room response of a large room can be greater than 1 second (48000 samples at 48 kHz sampling frequency). However, none of these early attempts have successfully optimized sound quality. In-fact, such audio conventional correction efforts have even worsened the sound quality in certain circumstances.

Most if not all room equalization systems design a black box correction system. For example, once the filters have been calculated, there is no user intervention. To the contrary, example embodiments of the present application allow for customized system design, which allows infinite user changes to the filters designed.

SUMMARY OF THE INVENTION

One embodiment of the present application may include a method of processing an audio signal, the method may include recording the audio signal generated within a particular room environment. The method may also include processing the audio signal to create an original frequency response based on the audio signal, creating at least two iterative filters based on at least two separate frequency ranges of the original frequency response, calculating an error difference between the frequency response modified by the at least two iterative filters and the original frequency response, and applying the error difference to the audio signal.

Another example embodiment of the present application may include an apparatus configured to process an audio signal, the apparatus may include a memory and a microphone configured to record and store an audio signal in the memory generated within a particular room environment. The apparatus may also include a processor configured to process the audio signal to create an original frequency response based on the audio signal, create at least two iterative filters based on at least two separate frequency ranges of the original frequency response, calculate an error difference between the frequency response modified by the at least two iterative filters and the original frequency response, and apply the error difference to the audio signal.

Another example embodiment may include a method of processing an audio signal. The method may include recording the audio signal generated within a particular room environment, processing the audio signal to create an original frequency response based on the audio signal, identifying a target sub-region of the frequency response which has a predetermined area percentage of a total area under a curve generated by the frequency response, determining whether the target sub-region is a narrow energy region, creating at least one filter to adjust the frequency response, and applying the at least one filter to the audio signal.

Another example embodiment may include an apparatus configured to process an audio signal. The apparatus may include a memory and a microphone configured to record the audio signal generated within a particular room environment. The apparatus may also include a processor configured to process the audio signal to create an original frequency response based on the audio signal, identify a target sub-region of the frequency response which has a predetermined area percentage of a total area under a curve generated by the frequency response, determine whether the target sub-region is a narrow energy region, create at least one filter to adjust the frequency response, and apply the at least one filter to the audio signal.

BRIEF DESCRIPTION OF THE DRAWINGS

FIG. 8 illustrates an example table of frequency modes, according to example embodiments.

DETAILED DESCRIPTION OF THE INVENTION

Figure 1A:
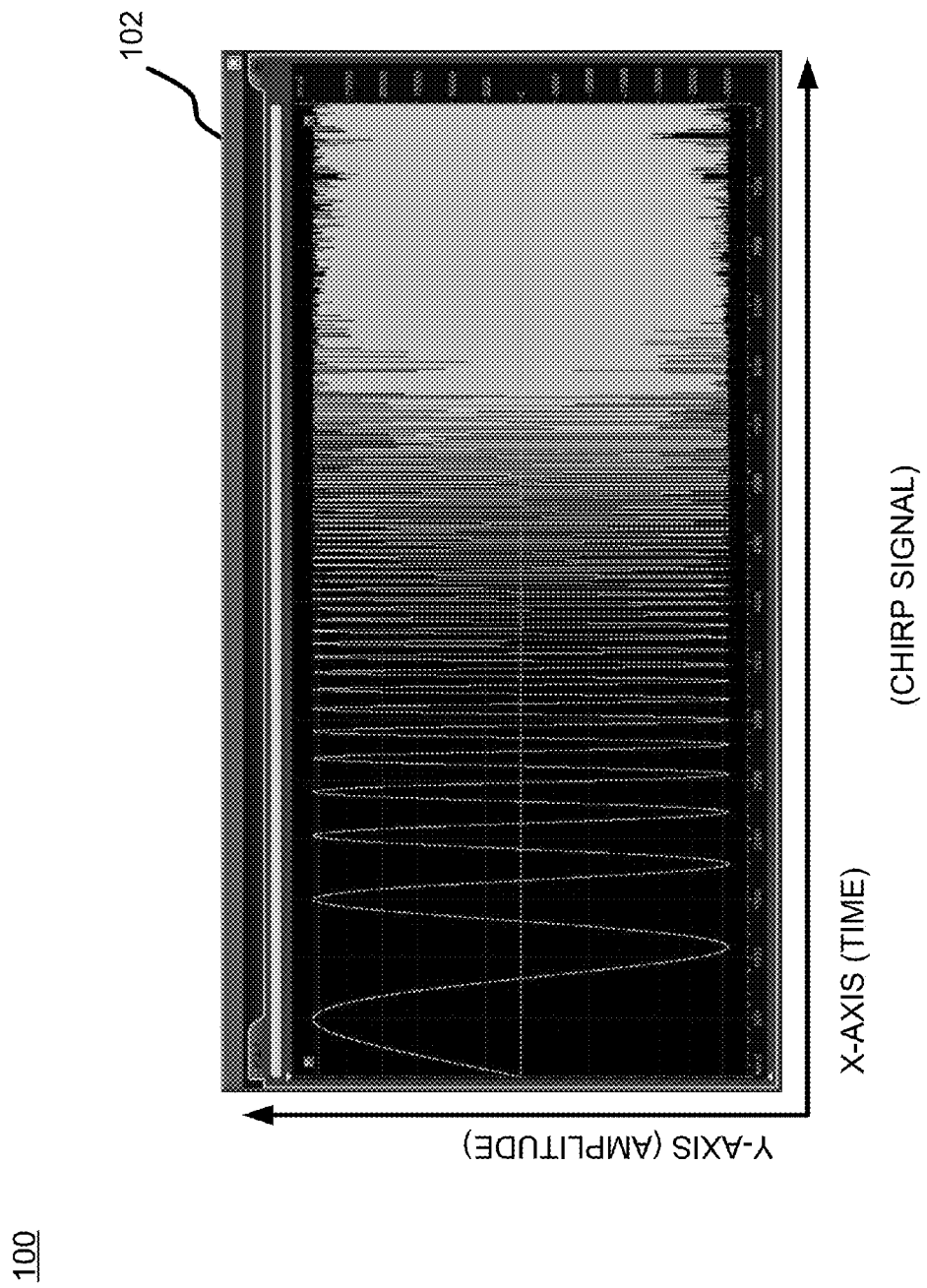
FIG. 1A illustrates an example plot of an original chirp audio signal as measured over time, according to example embodiments.

It will be readily understood that the components of the present application, as generally described and illustrated in the figures herein, may be arranged and designed in a wide variety of different configurations. Thus, the following detailed description of the embodiments of a method, apparatus, and system, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present invention. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present invention, the invention may be applied to many types of network data, such as, packet, frame, datagram, etc. For purposes of this invention, the term "message" also includes packet, frame, datagram, and any equivalents thereof. Furthermore, while certain types of messages and signaling are depicted in exemplary embodiments of the invention, the invention is not limited to a certain type of message, and the invention is not limited to a certain type of signaling.

Example embodiments provide efficient user adjustable audio room correction, calibration and feedback reduction for live environments in a reverberant room. Example algorithms and implementations of the audio correction techniques described in this specification describe a sophisticated algorithm that has been implemented on a digital signal processor (DSP) chip, such as the Texas Instruments DSP chip (TI-TMSC6747-375 MHz-DSP).

Example embodiments of may provide an algorithm that varies from simply inverting a room impulse response (IR). For instance, the algorithm used to adjust the audio of a particular room may first separate the impulse response into standing waves (low frequencies around the 200 Hz range), which also corresponds with the low limit of the speech frequency range and the diffuse field (i.e., above the Schroeder's frequency range).

According to one example, a one second unsmoothed room response would require up to a 48000 point finite impulse response (FIR) to fully equalize. This is a substantial amount of processing and if implemented as a time domain FIR, it may not be possible with the current capability of a single DSP chip or computer. An alternative implementation using IIR filters could require about a 1000 stages for a warped IIR filter design with custom warping profiles and application to room response modeling and equalization. The 1000 stage IIR filter still operates outside the requirements of a real time system. A warped IIR design allows the filter order to reduce to as low as 128. However, a lower order model, whether a warped IIR or not, will try to fit the room response in a least squares sense and will have the same error in the low frequency region as the high frequency region. In addition, the use of 'boosting' the frequencies has been shown to be detrimental to the sound quality.

A ⅙ octave smoothing of the room response could require a maximum of 66 IIR filters to equalize. However, "66" is still a large number as multiple channels of audio need to be equalized. A more appropriate number may be 10 stages, but 10 stages of filtering could be enough for certain room responses but most likely would be an under-fit to most rooms in general. Reducing the signal peaks more than the dips, a 10-stage IIR may make a good fit to the room response correction efforts.

According to one example implementation of the audio adjustment algorithm of the present application, a series of operations may include a detection phase that provides a test signal generation and room response recording, an analysis phase that include a 3 dB/Octave correction, a minimum phase conversion and a microphone compensation operation. Other operations may include removing reflections, smoothing on a log Frequency scale (⅙ Octave), and a multi-position averaging function. Additional operations include a filter design implementation that provides a user target response, a standing wave separation (Schroeder's frequency) and a separation of signal components into peak and dips.

Figure 7:
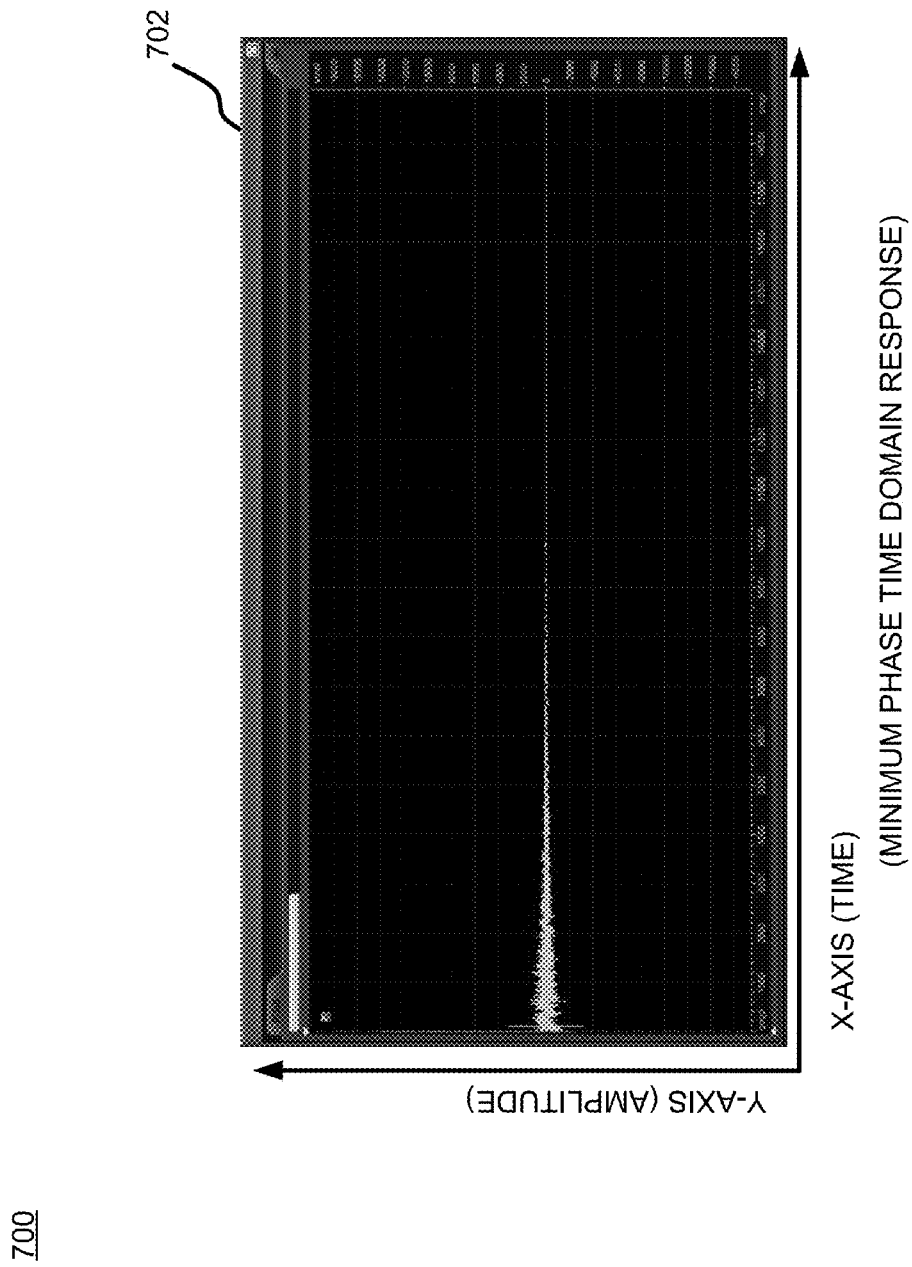
FIG. 7 illustrates an example plot of a minimum phase time domain response, according to example embodiments.

When the room EQ measurement is performed it represents the full impulse response of the room as illustrated in FIG. 7. The main peak at time=0 seconds corresponds to the direct sound from the sound source to the microphone as well as some smaller peaks a short time later. The smaller peaks represent the reflections of the room. The first sound to reach the microphone is always the direct sound. Next, the sound reflected off the floor and/or a wall arrives next at the receiver since the microphone is typically closer to the floor than any wall or ceiling. Multiple reflections from the walls, ceilings and floor build-up and form the impulse response of the room. The higher frequencies typically become absorbed in the walls and carpeted floor better than lower frequencies, as can be observed from the impulse response. The sound reflections which are within the first 50 ms (milliseconds) of the direct sounds are referred to as early reflections. Early reflections are not heard as separate sounds, and thus have a significant influence on how people may hear sound in a room. Reflections that reach the microphone after the early reflections are much closer together and are called late reflections or reverberations. In actuality, as the human ear uses the precedence effect (i.e., first 50 ms are averaged out to obtain a frequency response of the room). The late reflections should be windowed out so they have minimal influence in the room EQ calculation.

An iterative design is used to obtain low frequency and high frequency bands, the order of the filter, the peaks and the dips. This process must be repeated until all the filters are exhausted or the error criteria is satisfied. The implementation may include a low noise IIR architecture required because of large frequency range correction possibilities and to process room correction and feedback reduction (e.g., swapping filters as required).

In order to detect the room response the audio system needs to be excited by a test signal. The test signal should have finite energy in the frequency of interest. There are a wide variety of candidates for this type of test signal. These include stepped sine waves, chirp signals, maximum length sequence (MLS) signals, white noise, pink noise and impulse signals. According to example embodiments, a log chirp signal is used because of the good peak-to-average ratio as well as immunity to non-linear speaker distortion skewing the results. Longer lengths of the chirp produce higher S/N ratios of the measurements. The chirp length should be at least equal to the impulse response of the room as truncation of the measurement will lead to inaccurate results in the low frequencies. Typically, a one second chirp is used in room measurements as the impulse response, and in a conference room it can be about 0.8 seconds. The longer chirp length makes it increasingly difficult to work with as FFT sizes become very large for de-convolution or minimum phase conversion. Once the chirp is generated it has a very fast start and an abrupt end. This sudden start and end in a chirp signal is undesirable as it causes ripples in the frequency response.

FIG. 1A illustrates an example plot of an original chirp audio signal as measured over time, according to example embodiments. Referring to FIG. 1A, the original chirp signal 102 is illustrated over time in the graph 100. The chirp signal 102 has an undesirable ripple effect in the frequency response caused by the sudden start and end in the signal characteristics.

Figure 1B:
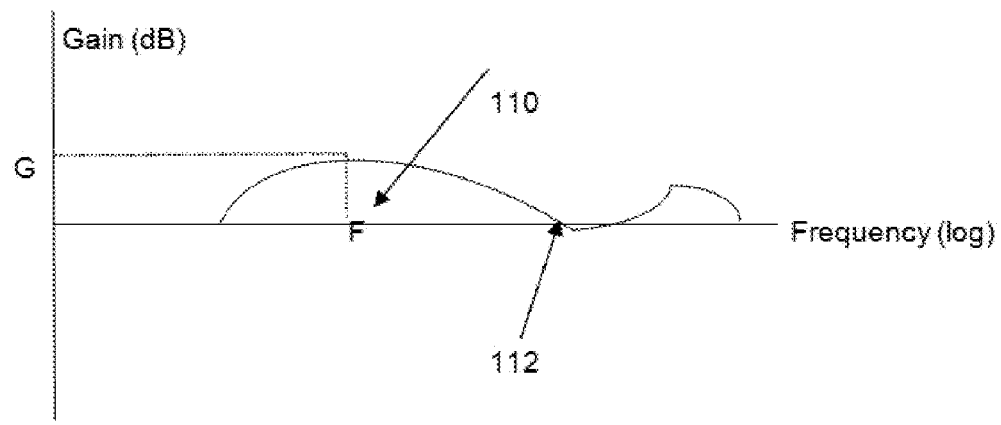
FIG. 1B illustrates an example plot of a target area of an original frequency response according to example embodiments.
Figure 1C:
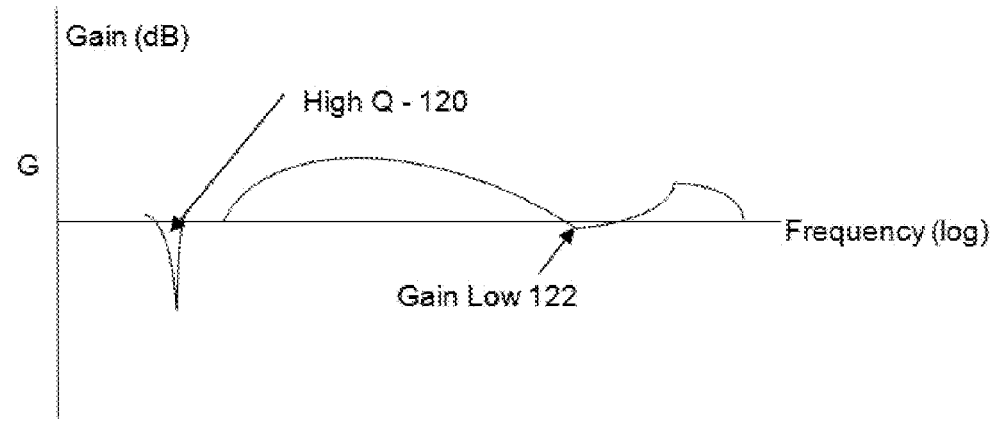
FIG. 1C illustrates an example plot of an original frequency response according to example embodiments.

FIG. 1B illustrates an example plot of a target area of an original frequency response according to example embodiments. Referring to FIG. 1B, the plot 130 illustrates a target area generated as a focused window of an original frequency response as illustrated in FIG. 1C. The largest area of the frequency response 110 is the area of interest where "F" is the center of the bell shaped curve, G is the height and Q is related to the center frequency (F) and the upper Hz indicated by 112 is derived below:

OctavesInvert=0.5f*log 10(2)/(log 10((float)upperHz/ (float)centerHz)); and Q=pow(2,1/(2*OctavesInvert))/(pow(2,1/OctavesInvert)−1).

Figure 1D:
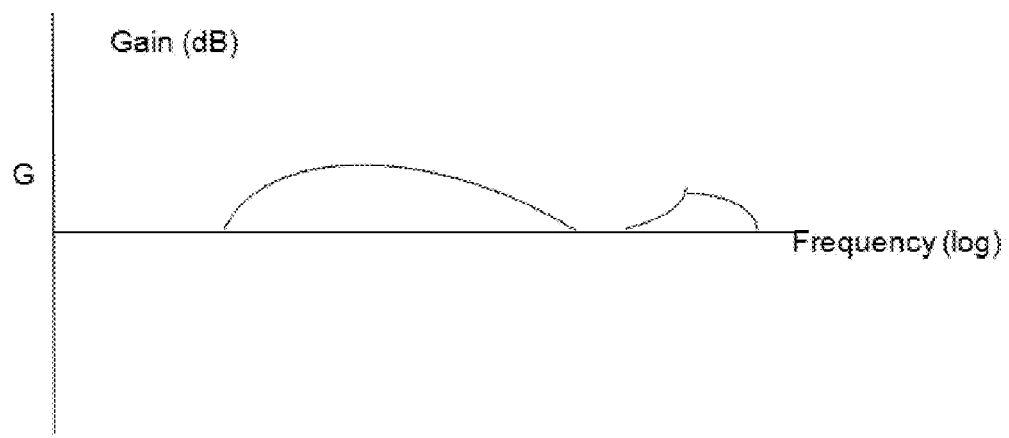
FIG. 1D illustrates an example plot of a new frequency response according to example embodiments.

FIG. 1C illustrates an example plot of an original frequency response according to example embodiments. In the original plot 140, the high Q 120 is illustrated as a dip that should be omitted. Also, the gain low 122 will need to be flattened or removed. FIG. 1D illustrates an example plot of a new frequency response according to example embodiments. The plot 150 has had the undesirable portions of the original plot 120 and 122 flattened to arrive at a new response with the high Q and low gain components removed.

Figure 2:
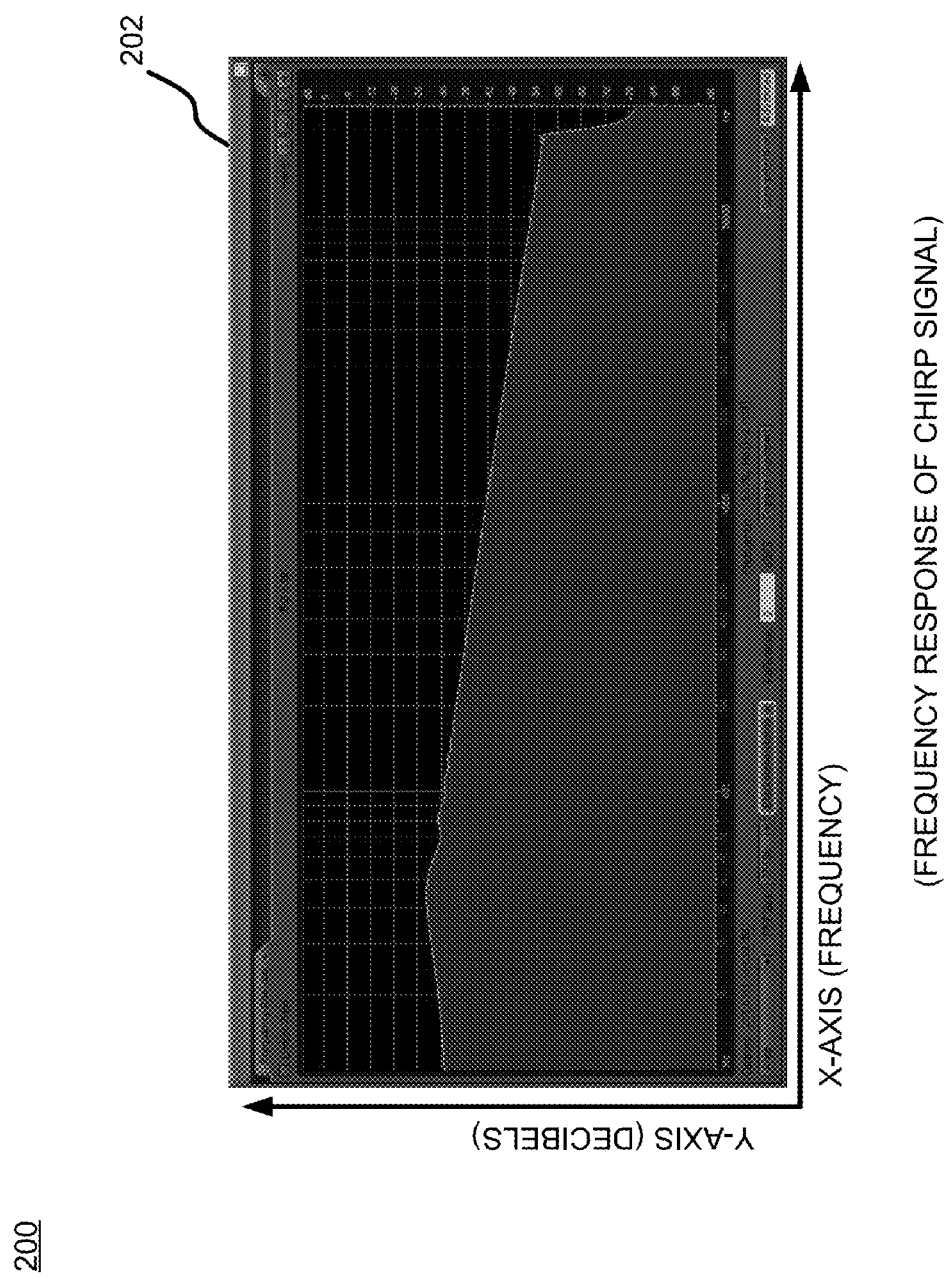
FIG. 2 illustrates an example plot of a frequency response of an original chirp audio signal, according to example embodiments.

FIG. 2 illustrates an example plot of a frequency response of the original chirp audio signal, according to example embodiments. Referring to FIG. 2, the frequency response 202 includes a gradual loss in power (dB) at the higher frequency ranges as shown in the plot 200.

To fix this undesirable ripple effect in the frequency response, the chirp signal is windowed with a tapered window function. Note, a shorter 8182 length chirp is shown due to the role-off in the low frequencies. The algorithm uses a 48000 (1 second) long chirp to perform its measurements.

Figure 3:
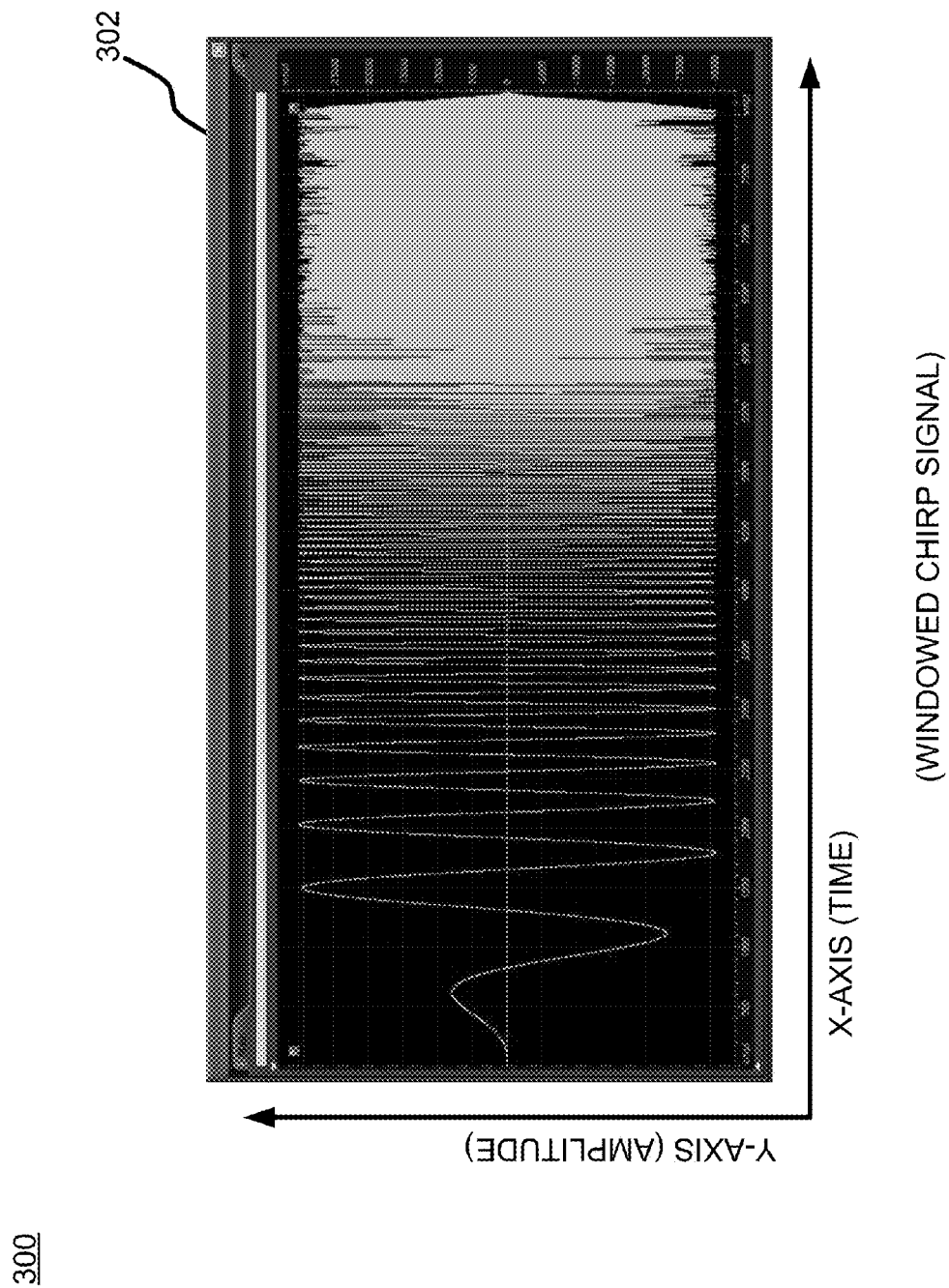
FIG. 3 illustrates an example plot of a windowed chirp audio signal as measured over time, according to example embodiments.
Figure 4:
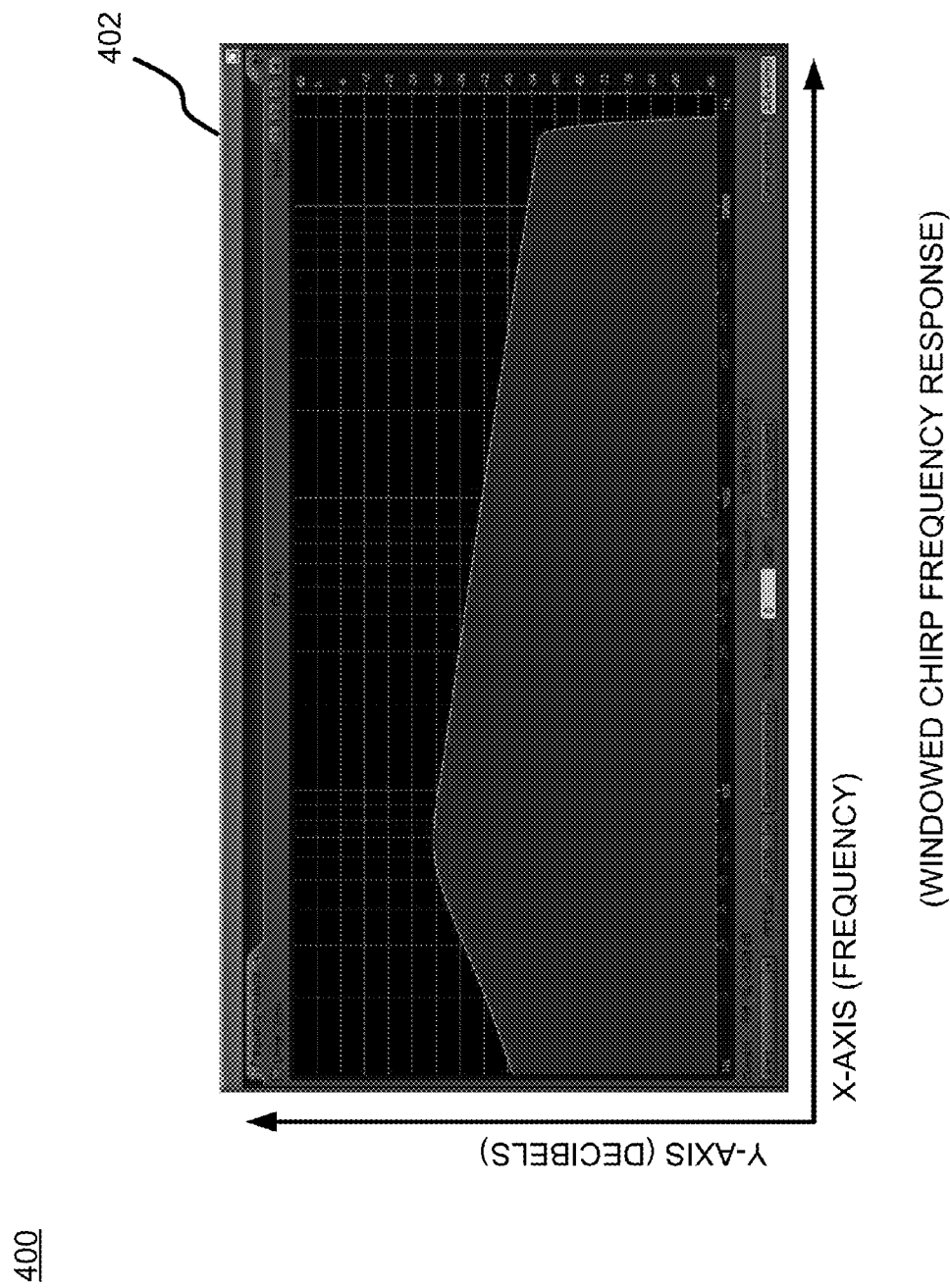
FIG. 4 illustrates an example plot of a windowed chirp frequency response, according to example embodiments.

FIG. 3 illustrates an example plot of a windowed chirp audio signal as measured over time, according to example embodiments. In FIG. 3, the plot 300 illustrates the windowed chirp signal with modified signal characteristics 302. FIG. 4 illustrates an example plot of a windowed chirp frequency response, according to example embodiments. Referring to FIG. 4, the plot 400 includes a log chirp frequency response 402 that falls at 3 dB/Oct. This is known as a pink frequency spectrum. The falling high frequency response stops high frequency damaging energy from being sent to a tweeter in the speaker.

Figure 5A:
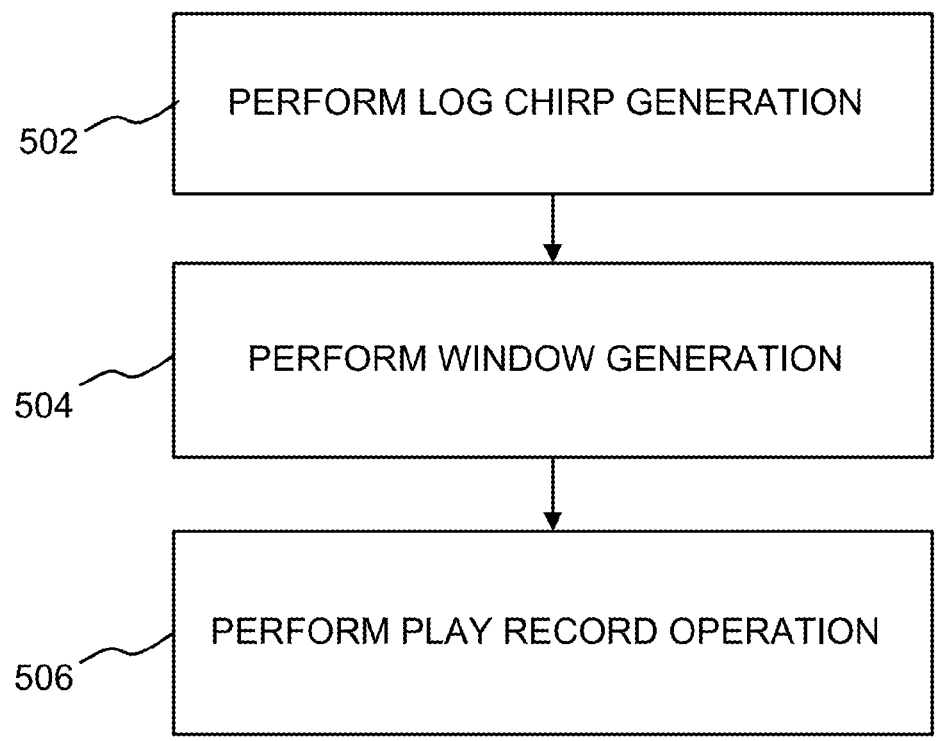
FIG. 5A illustrates a flow diagram of an example method of processing an audio signal, according to an example embodiment.

FIG. 5A illustrates a flow diagram of an example method of processing an audio signal, according to an example embodiment. Referring to FIG. 5A, the flow diagram 500 is an example method of performing a detection operation. The log chirp generator may generate a chirp signal at operation 502 and a pre-selected window may be applied to the chirp at operation 504. The room sound may then be recorded at operation 506 to determine a room acoustic profile or footprint that may be used for subsequent processing and correction purposes.

Figure 5B:
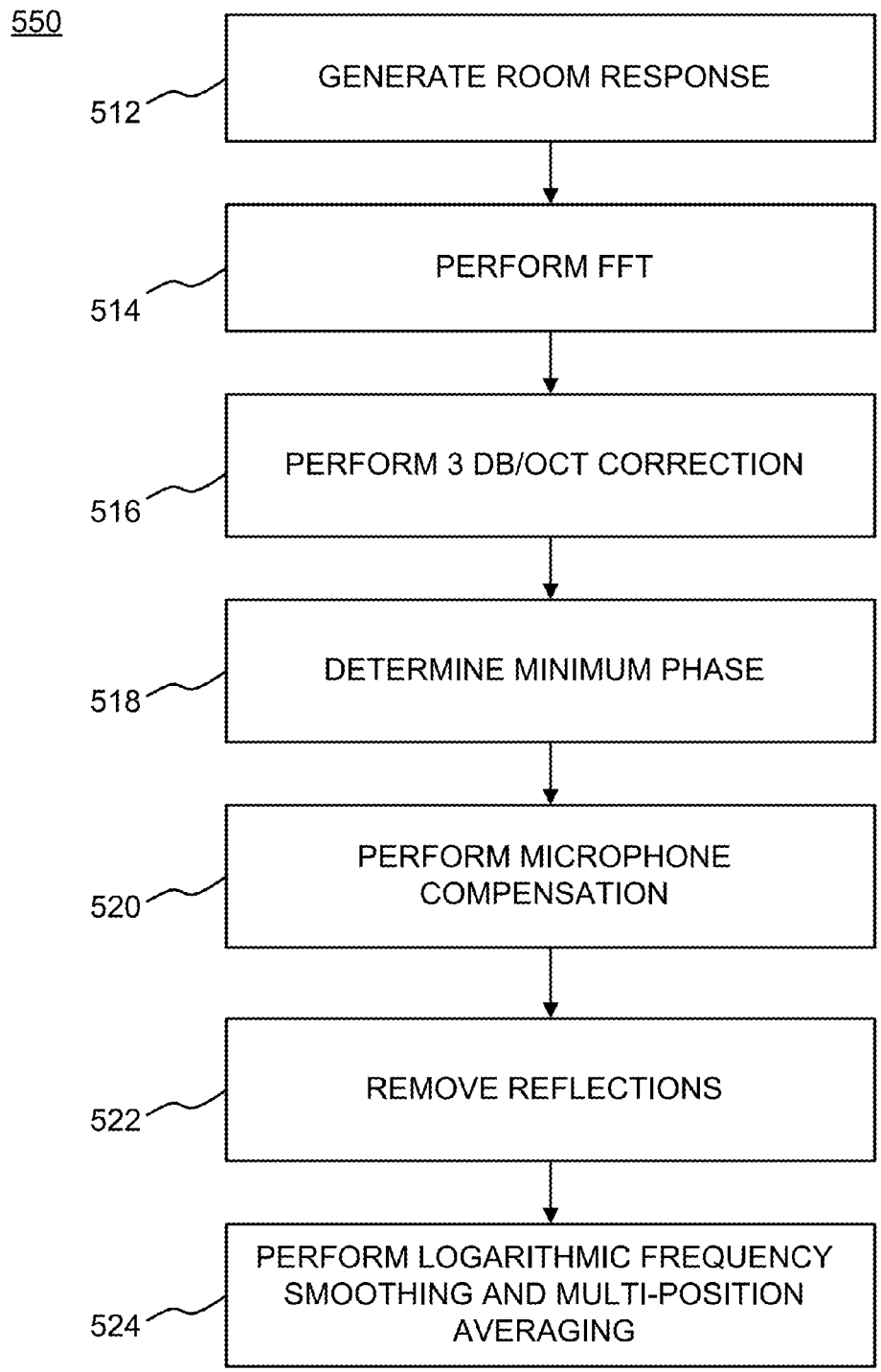
FIG. 5B illustrates a flow diagram of another example method of processing an audio signal, according to an example embodiment.

FIG. 5B illustrates a flow diagram of another example method of processing an audio signal, according to an example embodiment. Referring to FIG. 5B, once the chirp is played through the speakers and recorded for the length (time) of the original chirp. A 'raw' response of the room is then generated at operation 512.

Figure 6:
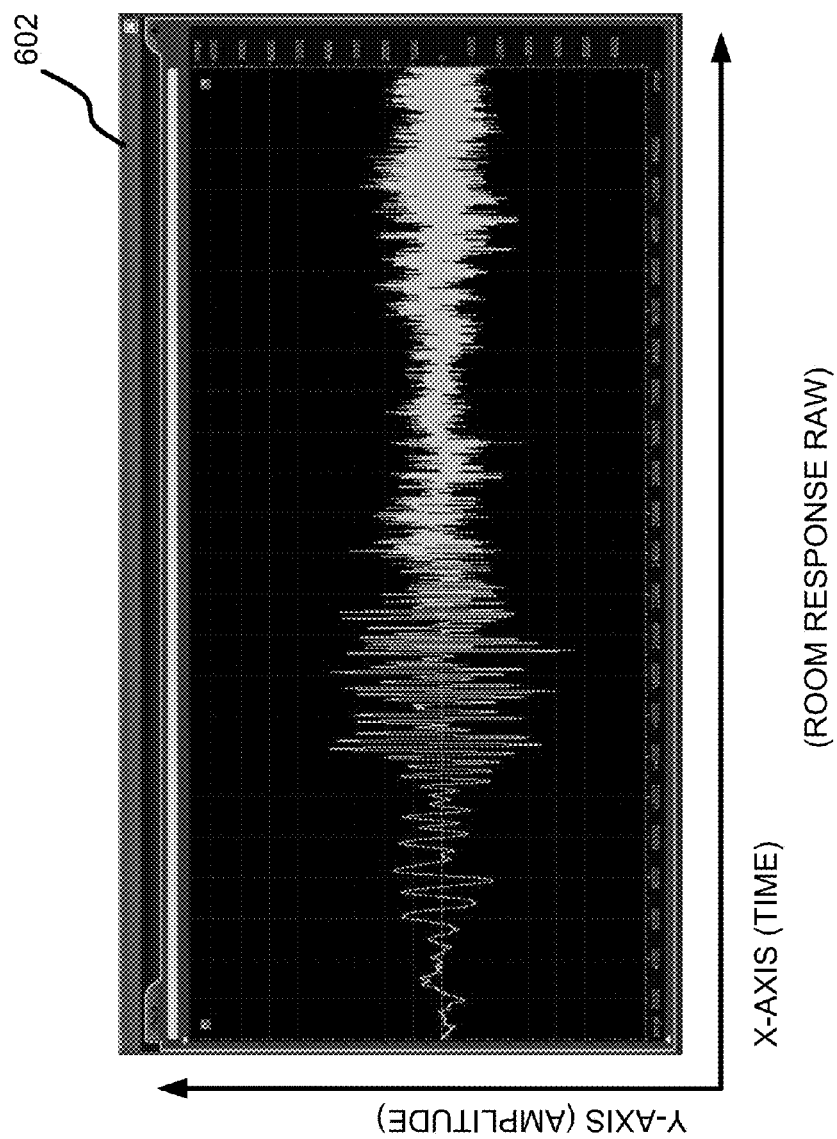
FIG. 6 illustrates an example plot of a raw room response as measured over time, according to example embodiments.

This signal is illustrated in the signal plot 602 of user interface 600 for FIG. 6. To convert this to the correct impulse response of the room, first the 3 dB/Oct correction operation must be performed at operation 516. This type of processing operation may be performed in the frequency domain. The raw signal is first converted to the frequency domain via a FFT operation 514. Then, the following equation is used to generate a 3 dB/Octave correction for the magnitude response:

FFT($n$)=FFT($n$)+10 log$_{10}$($n$); $n$=1,2 . . . ,Nyquist/2.

In order to determine the minimum phase at operation 518, the true room impulse response must be determined by deconvolving the processed signal with the original chirp signal. However, this operation may be unnecessary as the excess phase is negligible. The room has a minimum phase response, or can be approximated to a minimum phase response. As a result, instead the signal may be converted to a minimum phase. The minimum phase will also clearly demonstrate the recorded signal and reflections from the floor, ceiling and walls of the room. So for any room response H(w), this can be broken down into a minimum phase part and an all-pass part:

$$H(w)=H_{mp}(w)*H_{ap}(w).$$

To extract the minimum phase part, a nonparametric method of complex cepstrum may be employed. A large FFT size is used to reduce time aliasing errors. The accuracy of room correction is dependent on the frequency response of the microphone used for the measurement. Any variation in the microphone frequency response will lead to an inaccurate measurement. Correcting a room response with a microphone that is calibrated to +−0.5 dB from 20 Hz to 20 kHz would be ideal. A microphone compensation takes into account the variation in the frequency response of the microphone. For a microphone that is bundled with the product a correction is already built into the firmware. So a lower cost microphone could be bundled with this product which may have a non-flat frequency response without affecting the performance of the room EQ measurement and subsequent correction. As a result, the non-flat frequency response of the microphone as measured during room EQ is modified during the microphone compensation operation 520 to be F(corrected)=F(measured)−F(microphone). This is performed after the room measurement has been smoothed and adjusted to a minimum phase.

The plot 702 of minimum phase time domain response is illustrated in the GUI 700 of FIG. 7. The ideal microphone to record the measurement would be an omni-directional microphone with a ruler flat frequency response from 20 Hz to 20 kHz. As the cost of such a microphone is prohibitive a cheaper alternative may instead be used. However, its frequency response can vary from the ideal response as long as it is consistent for all microphones. A microphone compensation at operation 520, or a deviation from the ideal result is saved in the DSP and applied in the frequency domain.

Continuing with FIG. 5B, the impulse response of 1 second not only contains the direct sound but also the reflections. Sound perception at up to 'x' Hz is based on direct sound rather than the reflection. As a result, to design a more accurate correction only the direct sound plus the first few reflections should be used at operation 522. The windowing may be performed with a hamming window. In addition to removing late reflections, windowing also smoothes the frequency response. The windowed impulse response has several peaks and dips especially at the higher frequencies (see FIG. 9). As the wavelength at say 2 kHz is 6.7" (170 mm), any attempt at modifying very fine frequency peaks and dips will be unsuccessful because any correction is dependent on the position of the listener's head. Any slight movement, as small as 3", could result in a different tonal balance as the listener could move from a peak to a dip in the frequency response. A better approach to room correction is to correct fewer peaks and most dips at the lower frequencies and to correct out a soothed out region in the higher frequency range.

The ideal frequency response for a room is as flat as possible over the widest possible frequency range. However, most rooms dictate an uneven frequency response which can vary by as much as +/−20 dB. Perfectly equalizing such a room to a flat response is an unfavorable approach. First, at low frequencies where 20 dB frequency dips may exist, setting a filter of gain 20 dB will reduce an amplifier's headroom by 20 dB. Also it will drive the speakers into a more non-linear region if 20 dB of gain is added. The 20 dB gain correction will be correct at one particular position where the measurement was made but it may cause nulls, dips and/or peaks at different positions. Second, at high frequencies, an EQ unsmoothed high frequency region is also not a viable solution since the wavelength of high frequencies is very small (i.e., at 1 KHz the wavelength is 12"). So moving the microphone by a few inches to either side of the first measurement position may produce different results to equalize. So either a number of measurements at different positions have to be made and averaged or a good candidate for a target response is a logarithmically smoothed single measurement.

One way to attempt log smoothing 524 is using a warped IIR, but a warped IIR is not truly a logarithmic frequency resolution. Also the warped IIR solution attempts to fix peaks as well as dips. A better approach may be to smooth the frequency response on a logarithmic scale separating out the peaks and dips. A good compromise for frequencies above the Schroeder's frequency is achieved by using ⅙ octave since it is close to the critical bands in resolution. However, ⅙ Octave means a Q of 8.6. However ⅙ octave smoothing may be too high for the lower frequencies as a Q higher than 8.6 can exist in rooms. The Q of a room mode is dependent on the reverberation time. A highly reverberant room will have very high Q room modes. An approximation to the bandwidth is: $BW_{mode} \approx 2.2/T_{60}$. So for a typical conference room $T_{60}=1000$ msecs so the room mode $BW_{mode}=2.2$ which is equal to $BW=\log_2(f_u/f_c)$, where BW is the bandwidth in octaves, the $f_c$ is the center frequency and $f_u$ is the upper frequency. Hence the BW=0.077 Octaves, where Q=squareroot($2^{BW}$)/($2^{BW}-1$), and thus Q=18.7. The room response is separate into two parts with the separation around the Schroeder's frequency in order to equalize the room separately. If there are many room modes then they will combine into a smooth response rather than individual peaks of high Q. However, the combination is going to happen above the Schroeder's frequency. This will become clear with the equation for room modes for a rectangular room with length "L", width "W" and height "H":

$$f_{xyz}=c/2(\text{squareroot}((nx/L)^2+(ny/W)^2+(nz/H)^2))).$$

The values nx, ny and nz=0, 1, 2, and 3 are the half wavelengths between the walls. The value $f_{xyz}$ is the model frequency, and c is speed of sound. So the equation above includes very few modes below 200 Hz (i.e., discrete room modes).

For a specific example, modes for a room which is 16 ft×12 ft by 8 ft based on an equation table from the "Handbook for sound engineers" by Glen Ballou, considering the above-noted equation and the equation table (not shown), the number of modes increase with frequency as illustrated in table 800 of FIG. 8. As a result, the octave above 2500 Hz has over 350 room modes which blend into a smooth response.

Figure 9:
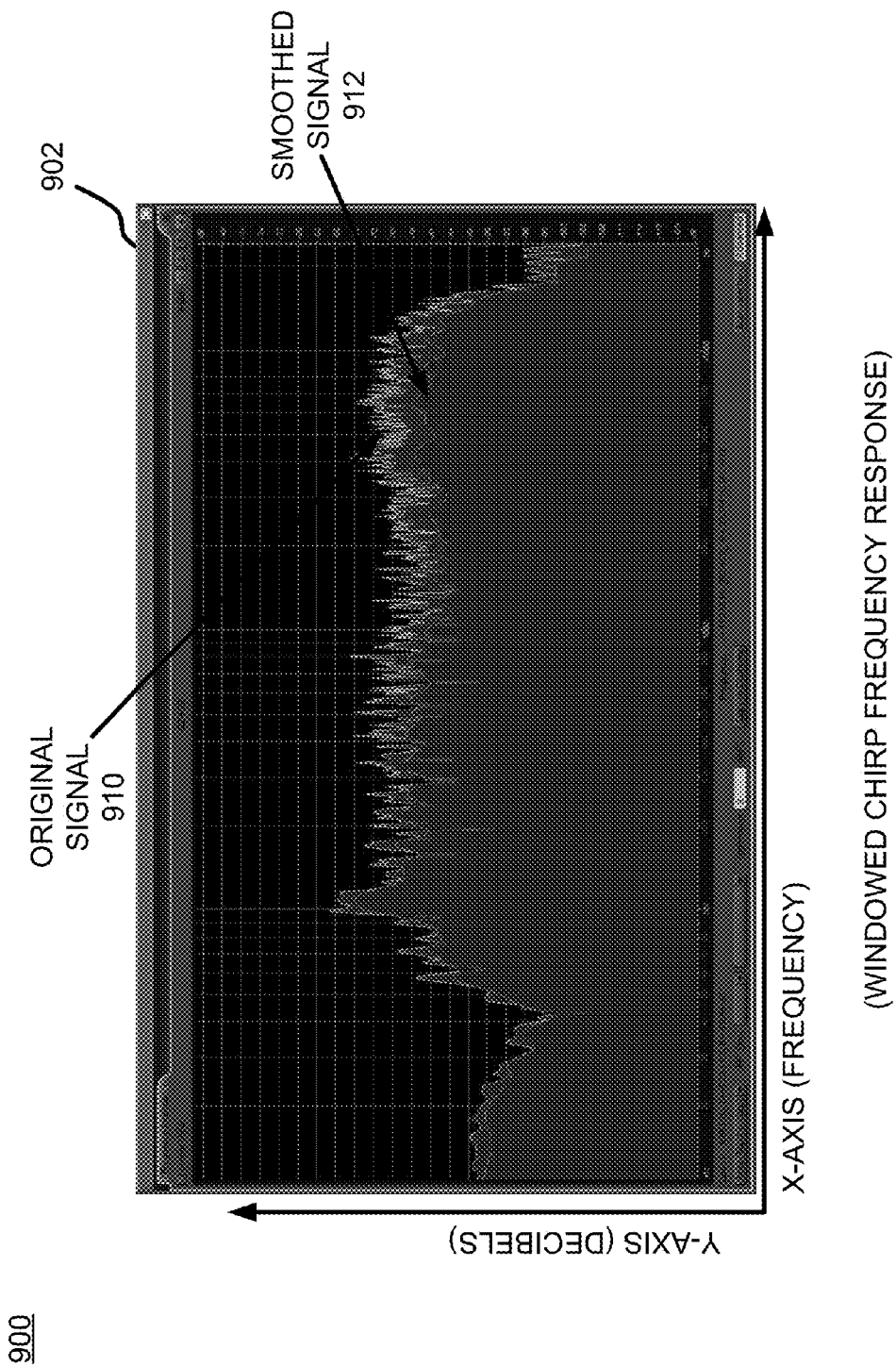
FIG. 9 illustrates another example plot of a windowed chirp frequency response, according to example embodiments.

FIG. 9 illustrates another example plot of an windowed chirp frequency response, according to example embodiments. Referring to FIG. 9, the user interface window 900 includes an original signal and a ⅙ log frequency smoothed (i.e., smoothed version) with a gain offset. The original signal 910 is illustrated as having many peaks and dips. The smoothed signal has had most of its peaks and dips smoothed out to have fewer transitions.

Figure 10:
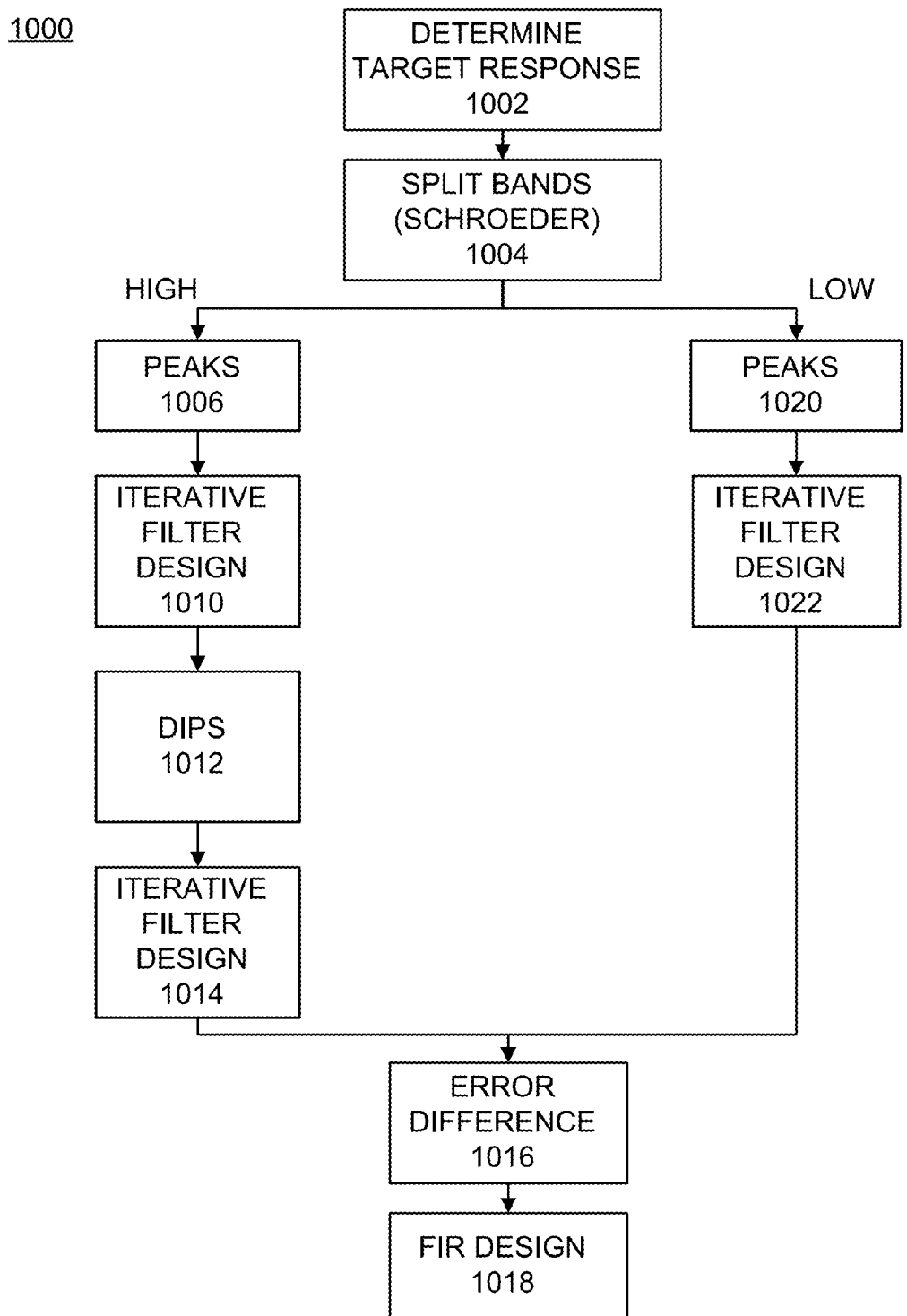
FIG. 10 illustrates an example flow diagram of using an audio sample to create an audio filter, according to example embodiments.

FIG. 10 illustrates an example flow diagram of using an audio sample to create an audio filter, according to example embodiments. Referring to FIG. 10, the flow diagram 1000 includes determining a target response 1002 which may be flat or any complex shape. Typically, a flat frequency response would be desired in a room environment but a flat response may not be ideal or produce the best sound. Regardless, any target response may be convolved with the log smoothed frequency response to produce a new frequency response to design. The target response is the actual room measurement derived using multiple criteria, such as multi-point averaging, minimum phase calculations, windowing, logarithmic smoothing, subtracting microphone reference signals, etc.

A frequency split may be performed to accommodate the Schroeder frequencies at operation 1004. This operation treats only the signal peaks at low frequencies. At higher frequencies, the signal peaks and dips may be equalized. According to example embodiments, the original target response is split into low and high frequencies with the split being at the Schroeder's frequency of the room. Most room EQ algorithms perform a full band correction, however, this approach is flawed for more than one reason. First, the whole frequency band is treated equally when it should be concentrated at the low frequencies. Second, the low frequencies being corrected by large-scale boosting can cause signal warping and overdriving of speakers. Some approaches incorporate a warped IIR approach which concentrates more filters for correction in the lower frequency band but provides loss of control or over correcting of peaks or dips as both are corrected equally.

The Schroeder frequency is $f_c=2000(squareroot(T_{60}/V))$. For a medium sized conference room (length=30', width=16', height=9'), $V=4320$ ft$^2$=(122 m$^2$), $f_c=2000(squareroot(1.0/122))=181$ Hz. Typical $T_{60}$ values may be for example, for a living room 500 msec and for a lecture/conference room 1000 msec.

Most if not all room correction algorithms design a correction by fitting a model onto the full frequency response. This model can be linear or warped (near logarithmic). However, boosting signals typically will lead to running out of amplifier power especially at the low frequencies where boosting may be >20 dB. In addition, peaks sound much worse then dips, and thus the peaks and dips are separated. One way to separate the peaks and dips 1006 and 1020 is to use a mean-square-error curve fitting in the frequency of interest combined with the low-frequency roll-off method. For the high frequency signal in operation 1006, the signal may have an extraction of the peaks above a reference that will be corrected first. For the low frequency signals in operation 1020, the signal may have its peaks extracted above a reference that will be corrected.

An iterative design may be used by operating in a log-frequency domain, and separating a signal into peaks and dips. Shanks is used as a model-order for the linear system. It is a least squares approximation and provides an indication on the target model-order. If the model order is high, then more filters may be allocated. The iterative IIR filter design 1010 and 1022 may be performed for peaks, dips and errors. The low frequencies (LF) and the high frequencies (HF) must be performed separately since a ⅙ octave (Q=9) would normally smooth the whole frequency response. The LF is modified by smoothing and the IIR design is performed for the LF then the HF with a 10 order IIR filter. These iterative filter design operations 1010, 1014 and 1022 are described in greater detail with reference to FIG. 11. In operation 1012, for the higher frequency signal, the dips may be extracted above a reference level. In operation 1016, an error or difference may be calculated between an original target response and a response of the filters designed using the iterative filter design. In operation 1018, a finite impulse response (FIR) filter design algorithm may be used to create an FIR filter based on the room sound data.

Figure 11:
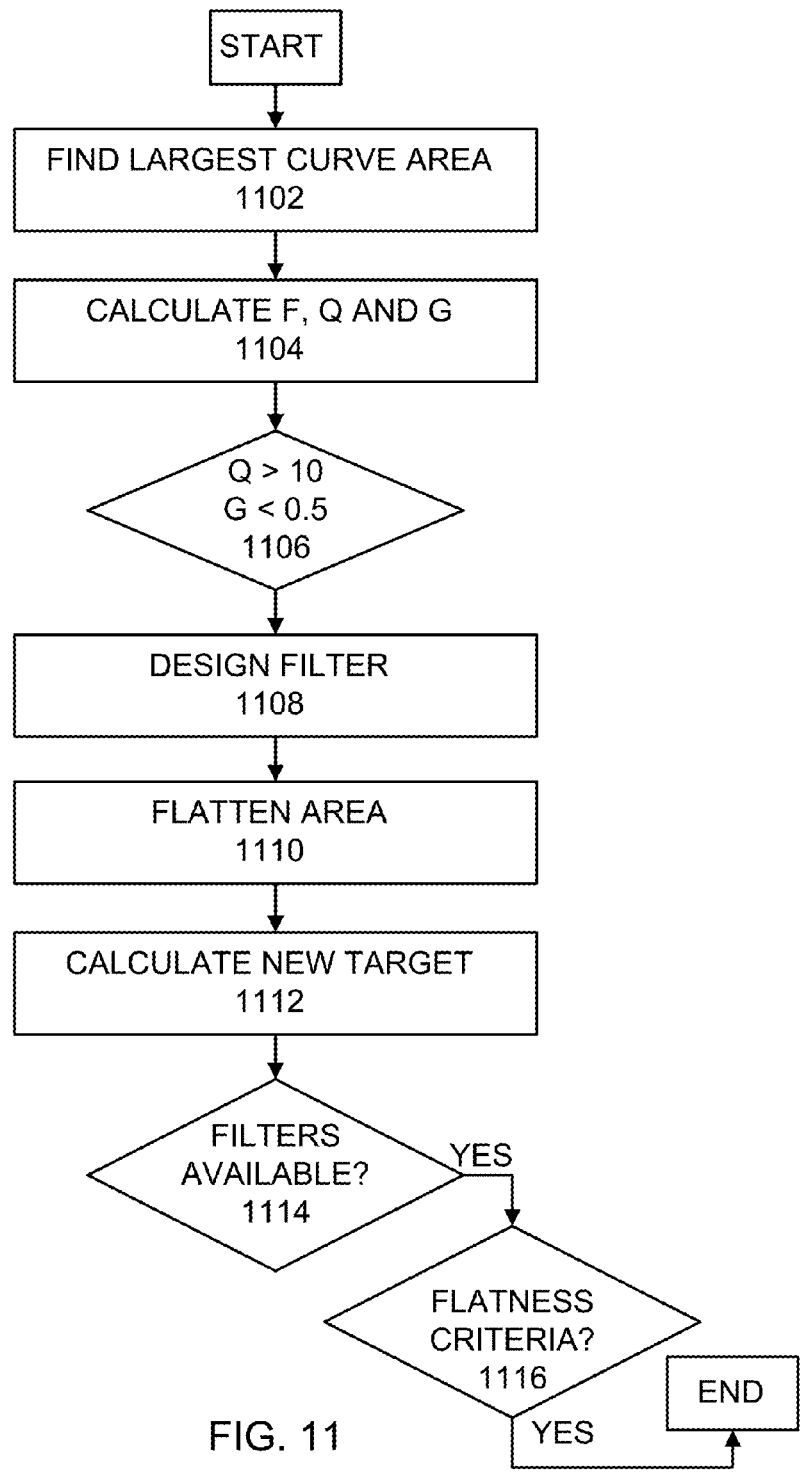
FIG. 11 illustrates another flow diagram of an audio filter creation process, according to example embodiments.

In order to achieve a useful set of room EQ filters an iterative process may be used. The audio signaling is highly non-linear and an exact solution may not exist. Another reason for implementing the iterative filter process is because an under-fitting optimization procedure is used to generate optimal audio characteristics. For example, a large number of filters could be calculated to obtain a precise solution to audio correction, but the DSP processing capability to implement such a solution is not endless. The iterative process allows the capability to target the correction where it is needed. FIG. 11 provides additional details of the iterative process. Basically, the iteration is performed to obtain a set of filters which will minimize the error where the error is identified as a least squares error weighted towards peaks and low frequencies.

An IIR can become unstable especially for a higher Q and a lower frequency. For a room correction and feedback reduction, a very high Q (Q>20) is possible an error feedback and 4-multiplier normalized lattice ladder may be used. One implementation selected is the 4-multiplier normalized lattice ladder. Not only does this architecture have low noise, it also has the added property of separating out the frequency (F), Q and gain (G) sections. If any one of the 3 independent variables (F, Q or G) are changed at a time, the filter experiences a minimal transient behavior and plots.

A target frequency response may be based on a room measurement. Typically, a room is not flat and has many peaks and dips. A target response is what is desired for the room response once the processing has finished. The target response may be flat but it does not have to be flat. For example, a room response may be slightly sloping as a response above 5 kHz. If the target response is flat then the room measurement may be captured and inverted. If the room has only 1 peak of 6 dB, with a Q of 1 at 2 kHz, but is flat everywhere else in the frequency response, then the target response for filter design purpose may be the measured response inverted. In one example, the frequency response of the target response will appear as a dip of Q=1 at 2 kHz. The filter design will include only one filter at a frequency of 2 kHz, a Q=1 and a g=−6 dB. Once that filter is designed the new target response is calculated by convolving the original target response with the response of the newly calculated filter. Convolution in the time domain is equal to multiplication in the frequency domain. Since the units of measurement are in dB, the original target frequency response may be subtracted from the newly calculated frequency response.

FIG. 11 illustrates another flow diagram of an audio filter creation process, according to example embodiments. Referring to FIG. 11, the flow diagram 1100 includes an operation to locate the region which has largest effect on the frequency response (e.g., largest area under the curve), at operation 1102. The flow diagram also provides calculating the frequency, Q and gain of the target region at operation 1104. If Q>10 and G<0.5 as determined at operation 1106 then there is a narrow energy region. The region may be flattened at operation 1110 via a flattening calculation. At operation 1108, a filter may be designed based on the new frequency, Q and gain values. The frequency response may be flattened if Q>10 and G<0.5 at operation 1110. At operation 1112, a new target may be calculated and the original target may be subtracted with the frequency response of the newly designed filter if they are available at operation 1114. Filter design may be stopped if the new EQ meets its predefined flatness criteria.

The FIR design procedure is an additional operation to design a FIR filter based on the error F(T_FIR). It may be a few taps, (i.e., 20 taps) and in combination with the room EQ filters, which are IIR parametric filters, may produce an accurate room correction. An example design operation may be include a windowing of the impulse response. The target is identified by finding a region which has the largest energy such that the filter may be fitted there. Next, smaller energy areas may be targeted. The biggest chunks are observed when G is large and Q is small. If G=15 dB and Q=20, then a narrow dip in the frequency response may be ignored. In affect an area may be flattened (removed) which has a high Q. Also, too many dB of correction may be undesirable as this could lead to compression or overuse of the speaker drivers. So gain is also limited in speaker compensation. If a wide portion of the response having say Q=1 and gain=0.5, it may not be worth fitting into a filter. Everything that generates a Q<10 and G>0.5 may be used and F, Q and G may be calculated accordingly. The F, Q and G define a parametric bell filter.

Once a portion of the response is identified, it is assumed to be bell-shaped. This is a reasonable assumption because the non-flat frequency response of the room is caused by reflections from the walls and ceiling of the room and these have a certain Q and decay. If the shape is more complex than a bell than more than one filter will be designed in that particular area. So once this portion is identified, its frequency is the center of the peak, gain is the height and Q is OctavesInvert=0.5f*log 10(2)/(log 10((float)upperHz/(float) centerHz)); // 1/octavesQ=pow(2, 1/(2*OctavesInvert))/(pow(2, 1/OctavesInvert)−1); where a center Hz is the point where the peak of the portion is at its maximum, upper Hz is the top of the frequency of the portion where it ends. Any target response is broken down into areas to be flattened. Any area that is too narrow (high Q) or too shallow (low gain) is removed/flattened. For example, FIG. 1D illustrates a new frequency response that has two areas that are removed leaving two major areas to fit filters. Note each area is not quite bell shaped and will require multiple filters to flatten. Once an area is deemed to have a high Q or is too shallow it is removed and another iteration of the algorithm is performed. The new frequency response becomes the target for the next iteration.

Figure 12:
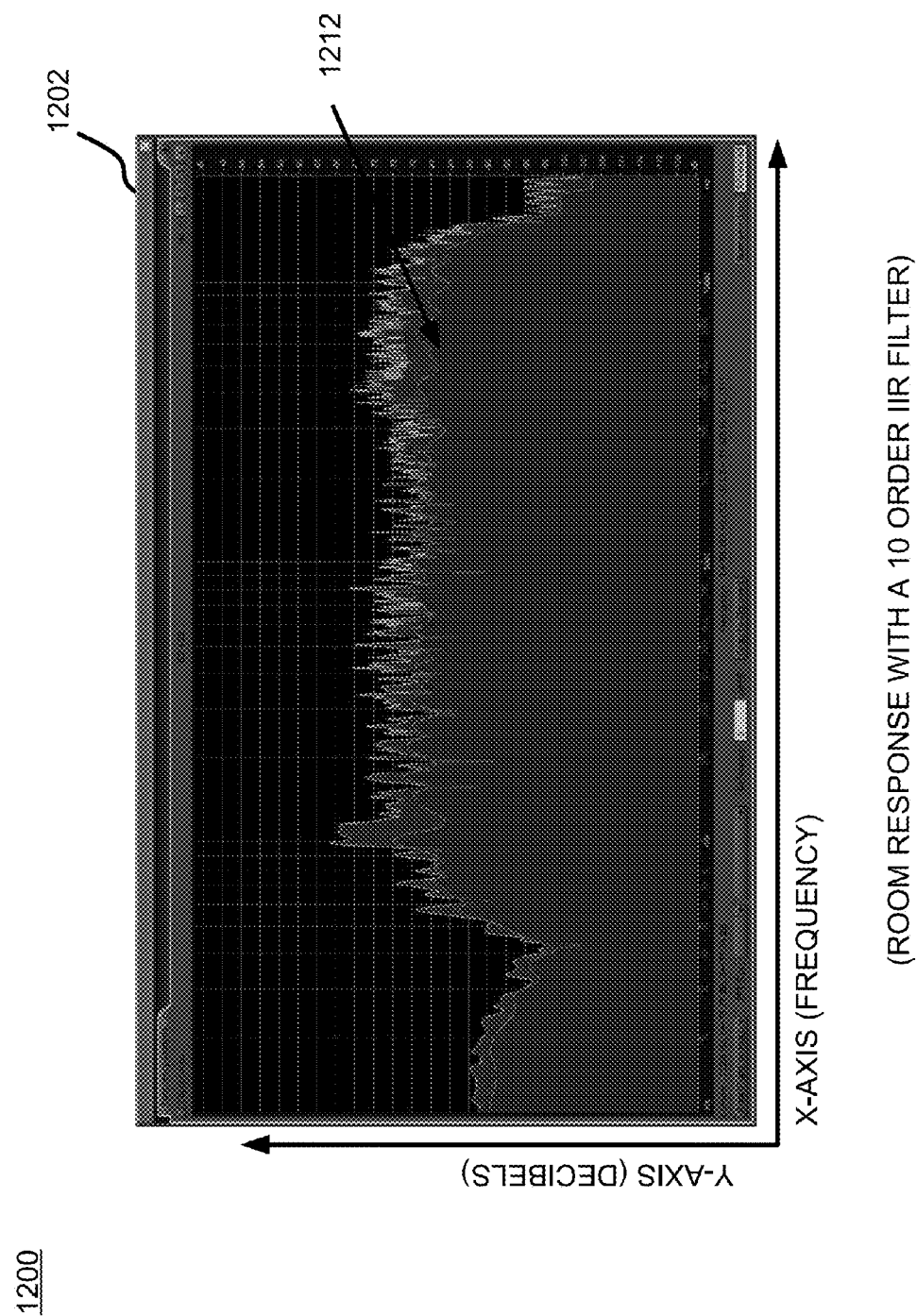
FIG. 12 illustrates a room frequency response with a 10 order IIR filter, according to example embodiments.

FIG. 12 illustrates a room frequency response 1200 with a 10 order IIR filter, according to example embodiments. FIG. 12 illustrates the original captured frequency response and the $10^{th}$ order IIR correction filter inverted response. The smoothed signal 1212 in the viewing window 1202 is smoother than the smoother signal 912 in FIG. 9. Referring to FIG. 9, the original captured frequency response and the smoothed minimum phase, windowed and log smoothed signals are illustrated. However, the $10^{th}$ order IIR correction filter provides an even smoother response signal when applied to capture audio signal.

Figure 13:
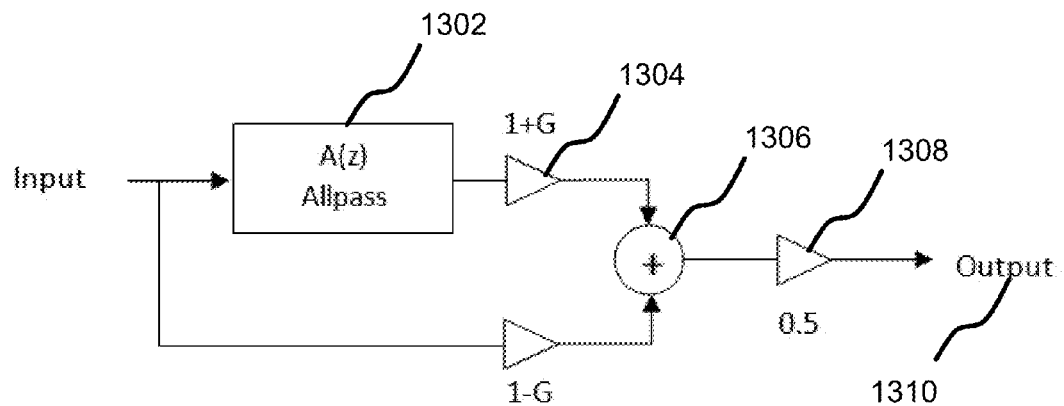
FIG. 13 illustrates an example lattice ladder architecture feedback system, according to example embodiments.

A normalized lattice ladder architecture when implemented as an all-pass section is illustrated in FIG. 13. Referring to FIG. 13, each filter of the room EQ is a parametric $2^{nd}$ order filter (biquad filter). There are a number of implementations possible for each biquad filter. One possibility for minimal noise and maximum stability is an allpass subsystem filter as illustrated in FIG. 13. The allpass filter is implemented as a 4-multiplier lattice-ladder filter. The configuration 1300 includes an allpass filter 1302, a multiplier 1304, adders 1306 and 1308 and an output of the filter 1310. For a 4-multiplier normalized ladder, the coefficients may be ramped. This reduces FB as the filters are constantly changing. FB reduction requires dynamic changes to the filter and it is important to minimize the effect of filter insertion, deletion and F/Q/G changing into the audio path.

A user may change the F, Q and G for adjustment purposes and to identify a desired output signal. As the filters are parametric and are graphically represented it makes it very easy to modify. Examples include moving between feedback and room correction (sharing filters). Feedback reduction (FBR) may be performed with a parametric filter having an all-pass filter, changing Q and a changing gain. Other features include FBR moving from parametric to notch, and FBR detection criteria.

Example embodiments provide an efficient IIR implementation for room correction which is user adjustable. Most peaks will be reduced and a few dips in a given room response. A unique room correction iterative filter design may be performed. A frequency selective band may be performed up to 200 Hz standing waves and high frequency. A high performance IIR architecture has low noise. A minimal transient behavior during a FB filter insertion and deletion operation may include an allpass IIR with a 4-multiplier lattice ladder filter and a unique FB reduction algorithm with parametric filters that becomes a band stop, and includes sharing filters and resources with a room calibration effort.

Figure 14:
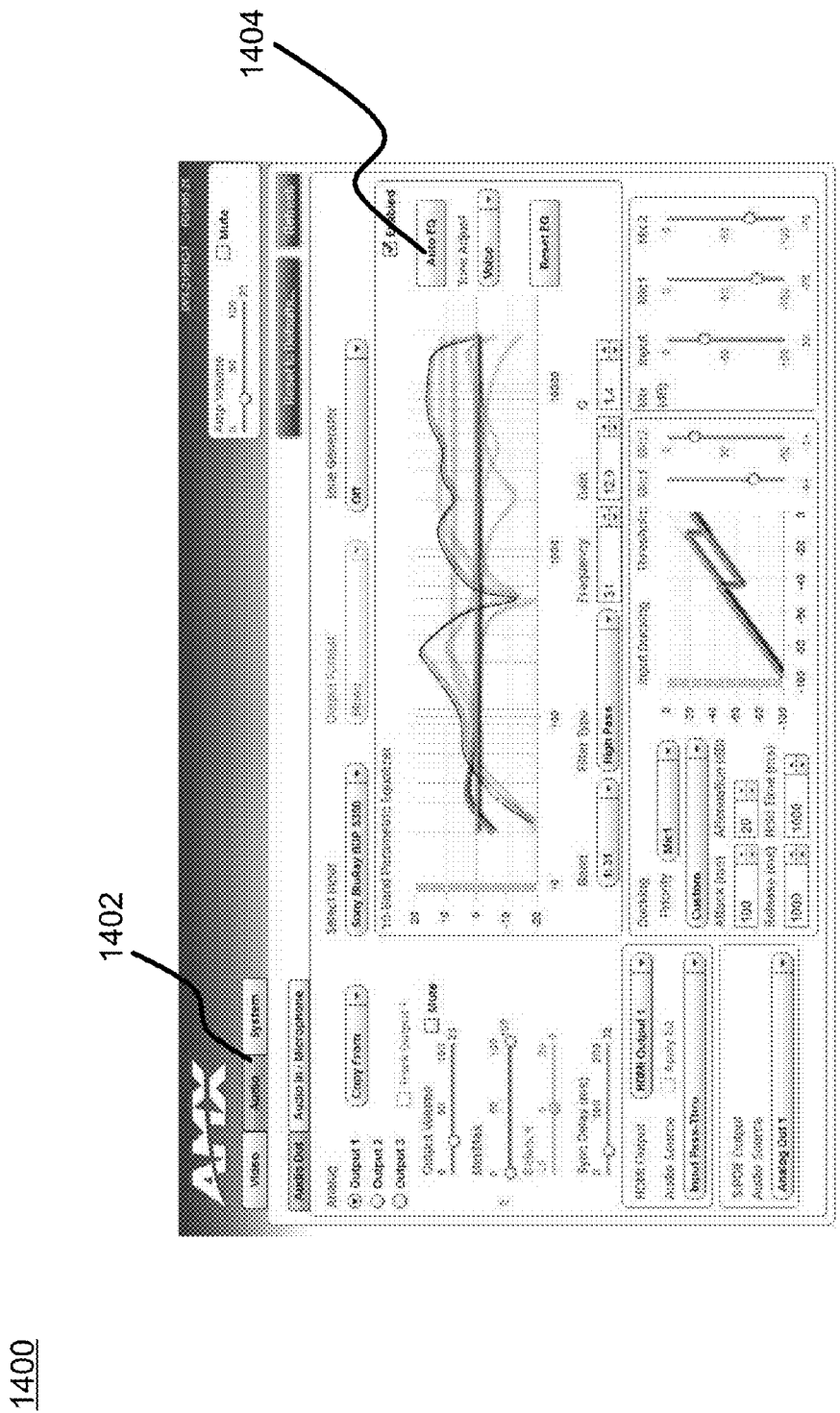
FIG. 14 illustrates an example graphical user interface allowing for customized user audio modification purposes, according to example embodiments.

FIG. 14 illustrates an example graphical user interface allowing for customized user audio modification purposes, according to example embodiments. Referring to FIG. 14, the graphical user interface 1400 provides various features and control functions that a user may select and execute to perform audio signal processing. For example, a user may select an option 1404 to automatically perform audio equalization (EQ) in the audio menu 1402. As a result, a connected microphone may be used to capture audio data and within 10 seconds of pressing the EQ button 1404, measurements may be taken and new filters may be calculated. The frequency response may be presented to the user and the calculated filters may be modified to adjust the frequency response. Also, an option to hear the difference between room EQ filtering and no EQ may be performed to observe the changes made by filtering and whether there was an overall improvement.

Figure 15:
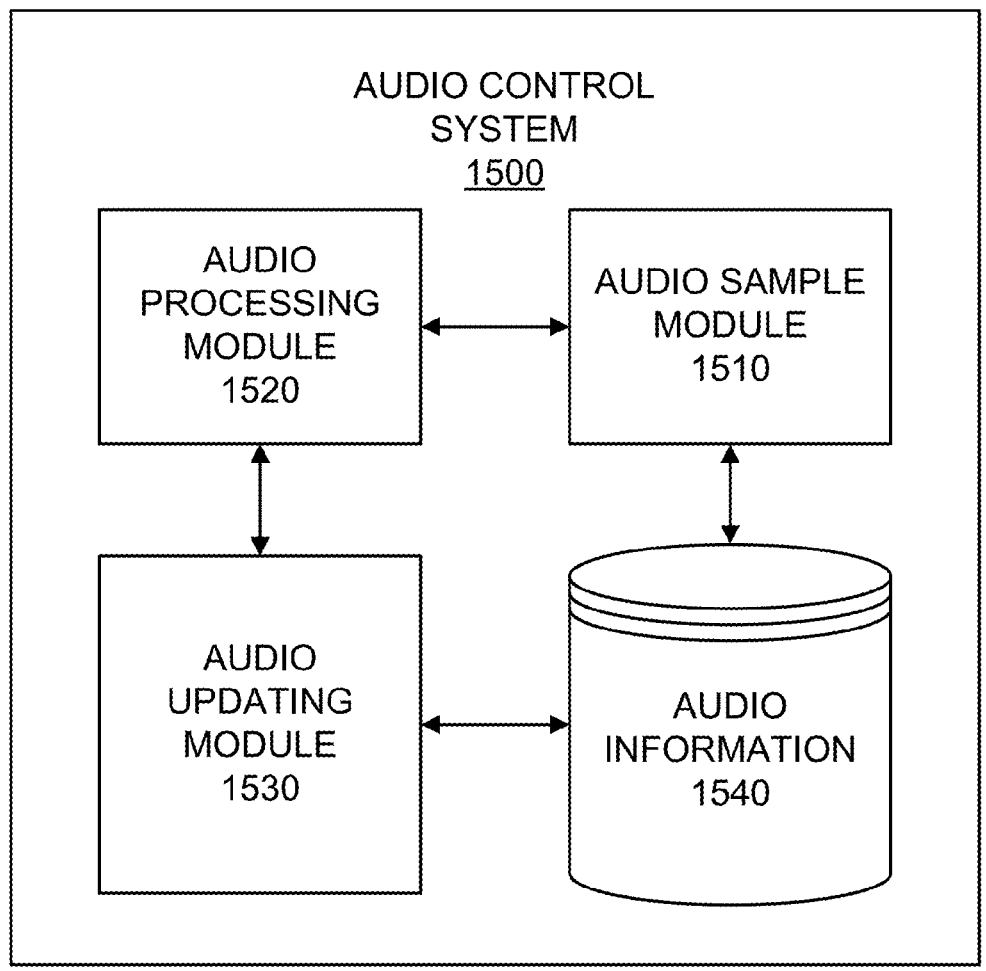
FIG. 15 illustrates an example audio control system, according to example embodiments.

FIG. 15 illustrates an example audio control system, according to example embodiments. Referring to FIG. 15, the audio control system 1500 may include various engines, modules, hardware components, etc., configured to process audio data and create a particular audio filter, response or corrective parameter(s) used to optimize an audio signal. One example method of operation of the audio control system may include a method of processing an audio signal by recording the audio signal generated within a particular room environment. The room may be ideally a four walled room with a ceiling and floor and with no other openings other than a negligible-sized door that opens and closes. A sample audio signal may be played in the room and recorded via a microphone and stored in memory in a digital format. The audio information database or memory 1540 may store the recorded audio and provide it to the audio sample module 1510 which retrieves the audio sample, formats it and provides it to a processing module 1520 so the audio signal can be realized as an original frequency response based on the original audio signal. The processing module 1520 may also create at least two iterative filters based on at least two separate frequency ranges of the original frequency response as illustrated in FIG. 10. The processing module 1502 may also calculate an error difference between the frequency response modified by the at least two iterative filters and the original frequency response and apply the error difference to the audio signal.

The original frequency response is generated based on an actual room measurement derived from at least one of multipoint averaging, minimum phase calculations, windowing, logarithmic smoothing, and subtracting microphone reference signals. Also, the original frequency response may be processed to separate a range of lower frequencies within the original frequency response from a range of higher frequencies within the original frequency response. The at least two iterative filters may be created as one or more first iterative filters for the range of higher frequencies and a second iterative filter for the range of lower frequencies.

The signal peaks of the original frequency response are used as the basis for creating the second iterative filter at the range of lower frequencies. However, both the signal peaks and dips are used when creating the first iterative filter design at the range of higher frequencies.

Additionally, the finite impulse response (FIR) filter may be created based on the calculated error difference between the frequency response modified by the at least two iterative filters and the original frequency response. Prior to any filter creation processes, the peaks and dips of the original frequency response signal may be separated by calculating a means-square-error curve fitting a frequency range of interest of the original frequency response. The range of interest may be a sub-region where the area under the cover is larger and which represents the majority of the signal energy. The processed audio filter may be stored in the audio information memory 1540 via the audio updating module 1530 and applied to all subsequent audio generated inside the room environment.

Regarding the error difference calculation and the other measured parameters and components, F(T)=Target Frequency response, F(L)=Low Frequency band of target response, F(H)=High frequency band of target response, F(Lcor)=Low Frequency correction, F(Hcor)=High Frequency correction, F(Lerror)=Low Frequency Error left over after correction (as correction is not perfect), F(Herror)=High Frequency Error left over after correction (as correction is not perfect), and F (T_FIR)=Target for FIR filter design.

Example Equations provide F(T)=F(L)+F(H), F(Lerror)=F(L)−F(Lcor), F(Herror)=F(H)−F(Hcor), and where the error difference (1016) is: F (T_FIR)=F(Lerror)+F(Herror). So after the iterative design for the low frequency and the high frequency region is finished, the error between the response of the correction filters and the original target response is calculated to be F(T_FIR).

Another example embodiment corresponding to system of FIG. 15 may include another method of processing an audio signal. Referring to FIG. 15, the example method may include recording the audio signal generated within a particular room environment and processing the audio signal to create an original frequency response based on the audio signal and storing the audio signal and frequency response in the audio information memory 1540. The audio sample module may retrieve the audio signal and identify a target sub-region of the frequency response which has a predetermined area percentage of a total area under a curve generated by the frequency response. For example, the target sub-region may be represent about ½ of the total frequency range, however, it may be over 75% of the total area under the curve since the energy is denser at the selected portion of the total curve. The method may also include determining whether the target sub-region is a narrow energy region and creating at least one filter to adjust the frequency response via the audio processing module 1520. The audio updating module 1530 may apply the at least one filter to the audio signal.

The method may also include calculating a frequency, a quality factor (Q) and a gain (G) of the target sub-region via the audio processing module 1520. It may be determined whether the Q is greater than a predefined Q threshold and whether the gain is less than a predefined G threshold, if the Q is greater than the predefined Q threshold and the G is less than the predefined G threshold then the target sub-region may be determined to be a narrow energy region. If the target sub-region is determined to be a narrow energy region then a flattening operation may be performed on the target sub-region to create a new flattened sub-region via the audio processing module 1520.

The example method may also include creating a filter based on a new frequency, Q value and G value of the flattened sub-region and also creating a new frequency response based on the new target sub-region and the corresponding filter.

Once the new frequency response is created, the original frequency response may be subtracted from the new frequency response. According to one example, the predefined Q threshold is 10 and the predefined G threshold is 0.5, however, other threshold values may be applied.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example FIG. 16 illustrates an example network element 1600, which may represent any of the above-described network components, etc.

Figure 16:
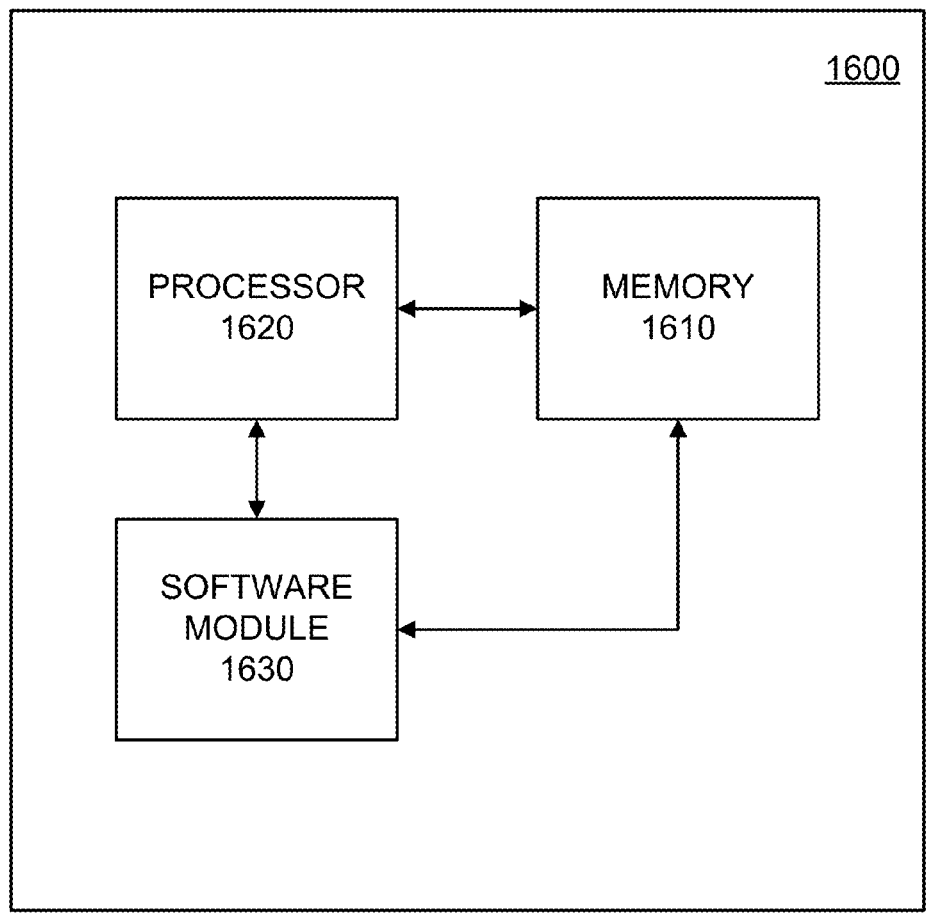
FIG. 16 illustrates an example network entity device configured to store instructions, software, and corresponding hardware for executing the same, according to example embodiments.

As illustrated in FIG. 16, a memory 1610 and a processor 1620 may be discrete components of the network entity 1600 that are used to execute an application or set of operations. The application may be coded in software in a computer language understood by the processor 1620, and stored in a computer readable medium, such as, the memory 1610. The computer readable medium may be a non-transitory computer readable medium that includes tangible hardware components in addition to software stored in memory. Furthermore, a software module 1630 may be another discrete entity that is part of the network entity 1600, and which contains software instructions that may be executed by the processor 1620. In addition to the above noted components of the network entity 1600, the network entity 1600 may also have a transmitter and receiver pair configured to receive and transmit communication signals (not shown).

While preferred embodiments of the present invention have been described, it is to be understood that the embodiments described are illustrative only and the scope of the invention is to be defined solely by the appended claims when considered with a full range of equivalents and modifications (e.g., protocols, hardware devices, software platforms etc.) thereto.

What is claimed is:

1. A method of processing an audio signal, the method comprising:
   recording the audio signal generated within a particular room environment;
   processing the audio signal to create an original frequency response based on the audio signal;
   identifying a target sub-region of the frequency response which has a predetermined area percentage of a total area under a curve generated by the frequency response;
   determining whether the target sub-region is a narrow energy region;
   creating at least one filter to adjust the frequency response; and
   applying the at least one filter to the audio signal.

2. The method of claim 1, further comprising:
calculating a frequency, a quality factor (Q) and a gain (G) of the target sub-region;
determining whether the Q is greater than a predefined Q threshold and whether the gain is less than a predefined G threshold; and
if the Q is greater than the predefined Q threshold and the G is less than the predefined G threshold then determining that the target sub-region is a narrow energy region.

3. The method of claim 2, wherein if the target sub-region is determined to be a narrow energy region then performing a flattening operation on the target sub-region to create a new flattened sub-region.

4. The method of claim 3, further comprising:
creating a filter based on a new frequency, Q value and G value of the flattened sub-region.

5. The method of claim 4, further comprising:
creating a new frequency response based on the new target sub-region and the corresponding filter.

6. The method of claim 5, further comprising:
subtracting the original frequency response from the new frequency response.

7. The method of claim 2, wherein the predefined Q threshold is 10 and the predefined G threshold is 0.5.

8. An apparatus configured to process an audio signal, the apparatus comprising:
a memory;
a microphone configured to record the audio signal generated within a particular room environment; and
a processor configured to
process the audio signal to create an original frequency response based on the audio signal,
identify a target sub-region of the frequency response which has a predetermined area percentage of a total area under a curve generated by the frequency response,
determine whether the target sub-region is a narrow energy region,
create at least one filter to adjust the frequency response, and
apply the at least one filter to the audio signal.

9. The apparatus of claim 8, wherein the processor is further configured to
calculate a frequency, a quality factor (Q) and a gain (G) of the target sub-region,
determine whether the Q is greater than a predefined Q threshold and whether the gain is less than a predefined G threshold, and
if the Q is greater than the predefined Q threshold and the G is less than the predefined G threshold then determining that the target sub-region is a narrow energy region.

10. The apparatus of claim 9, wherein if the target sub-region is determined to be a narrow energy region then the processor is configured to perform a flattening operation on the target sub-region to create a new flattened sub-region.

11. The apparatus of claim 10, wherein the filter is also configured to create a filter based on a new frequency, Q value and G value of the flattened sub-region.

12. The apparatus of claim 11, wherein the processor is also configured to create a new frequency response based on the new target sub-region and the corresponding filter.

13. The apparatus of claim 12, wherein the processor is also configured to subtract the original frequency response from the new frequency response.

14. The apparatus of claim 9, wherein the predefined Q threshold is 10 and the predefined G threshold is 0.5.

15. A non-transitory computer readable storage medium configured to process an audio signal, the processor being further configured to perform:
recording the audio signal generated within a particular room environment;
processing the audio signal to create an original frequency response based on the audio signal;
identifying a target sub-region of the frequency response which has a predetermined area percentage of a total area under a curve generated by the frequency response;
determining whether the target sub-region is a narrow energy region;
creating at least one filter to adjust the frequency response; and
applying the at least one filter to the audio signal.

16. The non-transitory computer readable storage medium of claim 15, wherein the processor is further configured to perform:
calculating a frequency, a quality factor (Q) and a gain (G) of the target sub-region;
determining whether the Q is greater than a predefined Q threshold and whether the gain is less than a predefined G threshold; and
if the Q is greater than the predefined Q threshold and the G is less than the predefined G threshold then determining that the target sub-region is a narrow energy region.

17. The non-transitory computer readable storage medium of claim 16, wherein if the target sub-region is determined to be a narrow energy region then performing a flattening operation on the target sub-region to create a new flattened sub-region.

18. The non-transitory computer readable storage medium of claim 17, wherein the processor is further configured to perform:
creating a filter based on a new frequency, Q value and G value of the flattened sub-region.

19. The non-transitory computer readable storage medium of claim 18, wherein the processor is further configured to perform:
creating a new frequency response based on the new target sub-region and the corresponding filter.

20. The non-transitory computer readable storage medium of claim 19, wherein the processor is further configured to perform:
subtracting the original frequency response from the new frequency response, and wherein the predefined Q threshold is 10 and the predefined G threshold is 0.5.

* * * * *